US008815272B2

(12) United States Patent
Woo et al.

(10) Patent No.: US 8,815,272 B2
(45) Date of Patent: Aug. 26, 2014

(54) RECYCLABLE POROUS BEAD—SATELLITE NANOPARTICLE COMPOSITE AND FABRICATION METHOD THEREOF

(75) Inventors: Kyoungja Woo, Seoul (KR); Hye Hun Park, Seoul (KR); Wooyoung Park, Daegu (KR)

(73) Assignee: Korea Institute of Science and Technology, Seoul (KR)

( * ) Notice: Subject to any disclaimer, the term of this patent is extended or adjusted under 35 U.S.C. 154(b) by 40 days.

(21) Appl. No.: 13/197,946

(22) Filed: Aug. 4, 2011

(65) Prior Publication Data

US 2012/0263777 A1 Oct. 18, 2012

(30) Foreign Application Priority Data

Apr. 12, 2011 (KR) ........................ 10-2011-0033923

(51) Int. Cl.

| | |
|---|---|
| ***A01N 25/26*** | (2006.01) |
| ***B82Y 30/00*** | (2011.01) |
| ***B82Y 40/00*** | (2011.01) |
| ***B03C 1/02*** | (2006.01) |
| ***B01D 43/00*** | (2006.01) |
| ***B01J 23/745*** | (2006.01) |
| ***B01J 23/755*** | (2006.01) |
| ***B01J 23/889*** | (2006.01) |
| ***B01J 21/08*** | (2006.01) |
| ***B01J 35/10*** | (2006.01) |
| ***B01J 23/50*** | (2006.01) |
| ***B01J 23/52*** | (2006.01) |

(52) U.S. Cl.

USPC ........... 424/421; 977/773; 977/904; 210/695; 502/300; 502/344; 502/347

(58) Field of Classification Search

None

See application file for complete search history.

(56) References Cited

U.S. PATENT DOCUMENTS

| | | | | |
|---|---|---|---|---|
| 2011/0059264 | A1* | 3/2011 | Park et al. | 427/510 |
| 2012/0212733 | A1* | 8/2012 | Kodali et al. | 356/301 |

FOREIGN PATENT DOCUMENTS

| | | | |
|---|---|---|---|
| CN | 101125968 | A | 2/2008 |
| JP | 6237030 | A | 2/1987 |
| JP | 02211262 | A | 8/1990 |
| JP | 5-504575 | A | 8/1992 |
| JP | 07171168 | A | 7/1995 |
| JP | 2003-522149 | A | 7/2003 |
| JP | 2006-502572 | A | 1/2006 |
| JP | 2009-509132 | A | 3/2009 |

(Continued)

OTHER PUBLICATIONS

Pankhurst et al., "Topical Review: Applications of magnetic nanoparticles in biomedicine", J. Phys. D: Appl. Phys., 36, Published Jun. 18, 2003, p. R167-R181.*

(Continued)

*Primary Examiner* — Tracy Vivlemore
*Assistant Examiner* — Monica Shin
(74) *Attorney, Agent, or Firm* — Ladas & Parry LLP

(57) ABSTRACT

An environment-friendly porous bead-satellite nanoparticles composite which has excellent recovery and repeated usage performance and can be used as a catalyst, an antiviral agent, or an antimicrobial, and a fabrication method thereof are provided. The porous bead-satellite nanoparticles composite includes a porous bead, a molecule having a first end coupled to the surface of the porous bead and including a functional group at a second end, and satellite nanoparticles coupled to the functional group, wherein the porous bead may have a core-shell structure including a cluster core of nanoparticles and a porous bead shell covering the cluster core.

17 Claims, 3 Drawing Sheets

(a) (b) (c)

(56) References Cited

FOREIGN PATENT DOCUMENTS

| | | | |
|---|---|---|---|
| KR | 1020090000859 | A | 1/2009 |
| KR | 1020100120904 | A | 11/2010 |
| WO | 2008/140624 | A2 | 11/2008 |

OTHER PUBLICATIONS

Ge et al., "Superparamagnetic Magnetite Colloidal Nanocrystal Clusters", Angew. Chem. Int. Ed. published 2007, 46, p. 4342-4345.*

Jana et al., "Synthesis of Water-Soluble and Functionalized Nanoparticles by Silica Coating", Chem. Mater., 19, Published on Web Sep. 17, 2007, p. 5074-5082.*

Lu et al., "Silver nanoparticles inhibit hepatitis B virus replication", Antivir Ther. 13(2), 2008, p. 1.*

Pradhan et al., "Silver nanoparticle catalyzed reduction of aromatic nitro compounds", Colloids and Surfaces A: Physicochem. Eng. Aspects, 196 (2002), p. 247-257.*

Erogbogbo et al., "Biocompatible Magnetofluorscent Probes: Luminescent Silicon Quantum Dots Coupled with Superparamagnetic Iron (III) Oxide", ACS Nano, vol. 4, No. 9, 2010, p. 5131-5138.*

Yan et al., "One-Step Seeding Growth of Magnetically Recyclable Au@Co Core-Shell Nanoparticles: Highly Efficient Catalyst for Hydrolytic Dehydrogenation of Ammonia Borane," J. Am. Chem. Soc. 2010, 132, p. 5326-5327.*

Polshettiwar et al., "Magnetically Recoverabl Nanocatalysts," Chem. Rev. published Mar. 14, 2011, p. 3036-3075.*

Narayan Pradhan, et al; "Silver nanoparticle catalyzed reduction of aromatic nitro compounds", Colloids and Surfaces A Physicochemical Engineering Aspects (2002), vol. 196, Issue 2-3, pp. 247-257.

Katherine C. Grabar, et al; "Preparation and Characterization of Au Colloid Monolayers", Analytical Chemistry (1995), vol. 67, Issue 4, pp. 735-743.

Jia Liu, et al; "Highly Water-Dispersible Biocompatible Magnetite Particles with Low Cytotoxicity Stabilized by Citrate Groups", Angewandte Chemie, Jul. 27, 2009, vol. 48, Issue 32, pp. 5875-5879.

Hye Hun Park, et al; "Core-Shell Bimetallic Nanoparticles Robustly Fixed on the Outermost Surface of Magnetic Silica Microspheres", Scientific Reports, 3: 1497; DOI: 10.1038/srep01497; Published Mar. 20, 2013; 7 pages.

Hye Hun Park, et al; *Supplementary experimental section and data for* "Core-Shell Bimetallic Nanoparticles Robustly Fixed on the Outermost Surface of Magnetic Silica Microspheres", Scientific Reports, 3: 1497; DOI: 10.1038/srep01497; Published Mar. 20, 2013; 13 pages.

Yonghui Deng, et al; "Multifunctional Mesoporous Composite Microspheres with Well-Designed Nanostructure: A Highly Integrated Catalyst System", Journal of The American Chemical Society, vol. 132, Issue 24, pp. 8466-8473; Jun. 23, 2010.

Chun-Liu Fang, et al; "Monodisperse $\alpha$-$Fe_2O_3$@$SiO_2$@Au core/shell nanocomposite spheres: synthesis, characterization and properties", Nanotechnology, vol. 19, No. 12, pp. 1-7; Published Feb. 21, 2008.

Jianping Ge et al; "Core-Satellite Nanocomposite Catalysts Protected by a Porous Silica Shell: Controllable Reactivity, High Stability, and Magnetic Recyclability", Angewandte Chemie International Edition, vol. 47, Issue 46, pp. 8924-8928; Article first published online Oct. 16, 2008.

James C. Y. Kah, et al; "Synthesis of gold nanoshells based on the deposition-precipitation process", Gold Bulletin, Mar. 2008, vol. 41, Issue 1, pp. 23-36.

Joo-Heon Lee, et al; "Synthesis of Nano-Colloidal Silica Coated with Silver", Journal Korean Ind. Eng. Chem. vol. 19, No. 1, Feb. 2008, pp. 45-50.

A. Penkova, et al; "Gold nanoparticles on silica monospheres modified by amino groups", Microporous and Mesoporous Materials, vol. 117, Issue 3, Available online Aug. 9, 2008, pp. 530-534.

Q.A. Pankhurst, et al "Applications of magnetic nanoparticles in biomedicine", Journal of Physics D: Applied Physics; vol. 36, pp. R167-R181; Published Jun. 18, 2003.

* cited by examiner

RECYCLABLE POROUS BEAD—SATELLITE NANOPARTICLE COMPOSITE AND FABRICATION METHOD THEREOF

FIELD OF THE INVENTION

The present invention relates to an environment-friendly porous bead-satellite nanoparticle composite which has excellent recovery and repeated usage performance and can be used as a catalyst, an antiviral agent, or an antimicrobial (or an antiseptic agent), and a fabrication method thereof.

DESCRIPTION OF THE RELATED ART

Unlike a material in bulk, nanoparticles exhibit unique physico-chemical characteristics due to the nano-size effect. In particular, compared with a bulk metal state having a large size, gold or silver nanoparticles exhibit remarkably improved anti-bacteria, deodorization characteristics, and performance as a catalyst, and iron oxide nanoparticles, semiconductor nanoparticles, or the like, have known to have an anti-biotic effect.

For example, silver nanoparticles having a size ranging from 10 nm to 50 nm has been reported to have an antibacterial effect against an HBV (Hepatitis B Virus) and suppressing multiplication of HBV particles [Antiviral Therapy 2008, 13, 253-262].

Also, gold or silver nanoparticles have been reported to have an excellent catalytic effect in a reducing reaction of aromatic nitro compounds into aromatic amine compounds under a presence of sodium borohydride ($NaBH_4$) as a reducing agent [Colloids and Surface A 2002, 296, 247-257].

Meanwhile, a nanoporous material such as silica ($SiO_2$), titania ($TiO_2$), zirconia ($ZrO_2$), alumina ($Al_2O_3$) has been known to have excellent adsorption capacity. The nanoporous material exhibits an antibacterial effect by adsorbing virus or bacteria, so research into the use of such a nanoporous material as a support has been attempted.

The nanoparticles presented above have a serious problem in that it is difficult to recover the nano-particles after the reaction is finished, although the nanoparticles have excellent performance as an antiseptic agent or as a catalyst. The nanoparticles discharged to the nature, rather than being recovered, cause hazardous effects to body and environment, so the recovery of the nanoparticles after the nanoparticles are used is critical task beyond the development of nanoparticles. Also, if high-priced noble metals such as gold and silver are recovered and repeatedly used, a high economical effect can be very high obtained.

Since the performance of nanoparticles are ascertained in various fields and the usage tends to be increased, a method for recovering and reusing nanoparticles as well as implementing the performance of nanoparticles is required, but has yet to be presented.

SUMMARY OF THE INVENTION

An aspect of the present invention provides an environment-friendly porous bead-satellite nanoparticle composite which can be applied for a catalyst reaction, an anti-microbial response, or the like, by effectively utilizing the characteristics of (satellite) nanoparticles on the surface of a porous bead by effectively coupling nanoparticles through molecules having a functional group to the porous bead and employing a core-shell structure, which have remarkably improved recovery and reuse performance, and which can be used as a catalyst, an antiviral agent, or an antimicrobial, and a fabrication method thereof. Also, problems of preceding studies can be overcome, a used composite can be entirely recovered through centrifugation or by providing a magnetic field after a catalytic reaction or an anti-microbial response, and repeatedly used, thereby solving an environmental hazard problem and improving economic efficiency.

According to an aspect of the present invention, there is provided a porous bead-satellite nanoparticles composite including a porous bead, a molecule having a first end coupled to the surface of the porous bead and including a functional group in a second end, and satellite nanoparticles coupled to the functional group, wherein the porous bead may have a core-shell structure including a cluster core of nanoparticles and a porous bead shell covering the cluster core.

According to another aspect of the present invention, there is provided a method for fabricating a porous bead-satellite nanoparticles composite, including: (a) introducing porous bead precursor materials to a first solution to prepare a second solution containing the porous bead; (b) introducing a molecule including a functional group at a second end to the second solution to combine a first end of the molecule to an outer surface of the porous bead to prepare a third solution containing a molecule-bonded composite; (c) introducing a satellite nanoparticle seed to the third solution to combine the satellite nanoparticle seed to the functional group of the second end of the molecule; (d) growing the satellite nanoparticle seed to prepare a fourth solution containing the porous bead-satellite nanoparticles composite; and (e) recovering the porous bead-satellite nanoparticles composite from the fourth solution, wherein a step of introducing porous bead precursor materials to the first solution containing a cluster of nanoparticles to prepare a second solution containing a composite including a cluster core of the nanoparticles and a porous bead shell covering the cluster core of the nanoparticles may be included instead of the step (a).

According to an embodiment of the present invention, a porous bead-satellite nanoparticles composite having a magnetic core and a porous bead shell and having nanoparticles which are uniformly and stably combined through a functional group of molecules bonded to the surface of the porous bead shell can be effectively fabricated in an area having a size ranging from tens of nm to a few μm.

The porous bead-satellite nanoparticles composite fabricated according to an embodiment of the present invention may be used as a catalyst in various organic reactions by utilizing the characteristics of the porous bead and the characteristics of the satellite nanoparticles and can be utilized to capture and remove virus and bacteria by using anti-bacteria, deodorization characteristics, or the like, of the nanoparticles.

According to an embodiment of the present invention, the porous bead-satellite nanoparticles composite can be easily recovered through centrifugation or by providing a magnetic field, and since the physico-chemical qualities of the nanoparticles on the surface of the composite are preserved even after the recovery of the porous bead-satellite nanoparticles composite, the porous bead-satellite nanoparticles composite can provide a material which can be repeatedly used, is environment-friendly, and economical. In particular, since the core is formed as a cluster of nanoparticles, the nanoparticles can be immediately responded to a magnetism so as to be easily recovered and re-used.

The foregoing and other objects, features, aspects and advantages of the present invention will become more apparent from the following detailed description of the present invention when taken in conjunction with the accompanying drawings.

DETAILED DESCRIPTION OF THE INVENTION

A porous bead-satellite nanoparticles composite according to an embodiment of the present invention includes a porous bead, a molecule having a first end coupled to the surface of the porous bead and including a functional group in a second end, and satellite nanoparticles coupled to the functional group. Since hundreds to thousands of satellite nanoparticles are coupled to the surface of a porous bead having a diameter of about 500 nm, the composite itself is sufficiently weighty so it can be easily separated through a low speed centrifugation and recovered. Also, since the porous bead-satellite nanoparticles composite can be easily separated by a commercial filter having pores smaller than 500 nm, the recovery and re-use efficiency of the porous bead-satellite nanoparticles composite can be enhanced.

Figure 1:
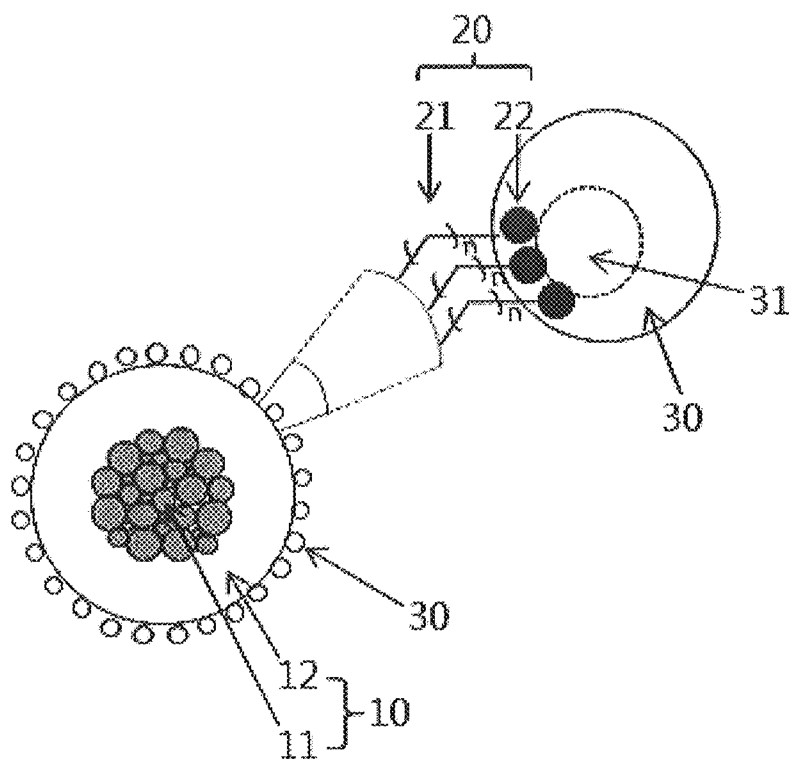
FIG. 1 is a schematic view of a porous bead-satellite nanoparticles composite according to an embodiment of the present invention.

The porous bead may have a core-shell structure including a cluster core of nanoparticles and a porous bead shell covering the cluster core. The nanoparticles constituting the cluster may be at least any one selected from the group constituting of FeO, $Fe_2O_3$, $Fe_3O_4$, $CoFeO_4$, $NiFeO_4$, $MnFeO_4$, Fe, Co, Ni, FeCo, and FePt, and the cluster core of the nanoparticles may have super-paramagnetism. FIG. 1 is a schematic view of a porous bead-satellite nanoparticles composite according to an embodiment of the present invention. A right upper portion in FIG. 1 shows a magnified coupling relationship between the porous bead shell and satellite nanoparticles through molecules having a functional group. As shown in FIG. 1, the porous bead-satellite nanoparticles composite includes a porous bead 10 comprised of a magnetic core 11 and a porous bead shell 12, molecules 20 coupled to the surface of the porous bead 10 and including a functional group, and satellite nanoparticles 30 coupled to the surface of the porous bead 10 through functional groups. Due to the super-paramagnetism of the cluster, when a magnetic field is provided, the cluster is well attracted to a magnet, but when the magnetic field is removed, the cluster is well dispersed in a solution. In an embodiment of the present invention, the nanoparticles cluster having super-paramagnetism is used as a core to allow the finally created porous bead-satellite nanoparticles composite to have super-paramagnetism.

In case in which one magnetic nanoparticle is used as it is in the core, if the thickness of the porous bead shell covering it is not large, an outer surface area of the porous bead shell is too small to allow a sufficient number of satellite nanoparticles to be attached thereto, while if the thickness of the porous bead shell is increased to attach a large number of satellite nanoparticles, the magnetic nanoparticles are not reacted to an external magnetic field. Thus, in an embodiment of the present invention, the core is configured as a cluster of magnetic nanoparticles. Also, in case of a single magnetic nanoparticle, since its magnetism is too weak, it take a long time to recover the nanoparticle with magnetic field, while when the cluster of the magnetic nanoparticles is used as a core, since the magnetism of the composite is strong, the composite can be recovered within a few minutes by using a magnetic field.

There is no limitation in the size or shape of the cluster core 11 of the nanoparticles, but preferably, the cluster core 11 of the nanoparticles has a diameter of 50 nm or greater, which is larger than that of the satellite nanoparticles 30 to be coupled to the porous bead 10, and 1 μm or smaller and has a spherical shape.

In the present embodiment, there is no limitation in the thickness of the porous bead shell 12 made of silica. However, if the thickness of the porous bead shell 12 is too large, its power attracted to magnetism weakens and the overall weight is increased, making it difficult to be recovered by using a magnet. Thus, preferably, the porous bead shell 12 has a thickness ranging from 2 nm to 1 μm.

The porous bead may be made of at least one selected from the group consisting of silica, titania, zirconia, alumina, and zeolite. Molecules having a functional group can be easily coupled to the surface of the porous bead, and an effect of improvement of the adsorption performance due to the porosity can be obtained. Also, the porous bead shell serves to physically protect the cluster core.

As the molecules having a functional group, which are coupled to the surface of the porous bead 12, a derivative of trialkoxysilane may be used. A carbon chain, one end thereof having a functional group, has 2 to 20 hydrocarbon atoms and the other end of the carbon chain is combined to trialkoxysilane. Thus, it can be easily combined to the surface of the porous bead by using a sol-gel method. When titania, zirconia, or alumina, instead of silica, is used as a material of the porous bead, a functional group can be provided to the composite by using a trialkoxy titanium derivative, a trialkoxy zirconia derivative, a trialkoxy alumina derivative. A function group of the second end may be at least any one selected from the group consisting of an amine group, a thiol group, and a carboxyl group.

The satellite nanoparticles may be multiple-bonded with the functional groups of the second end, and the satellite particles may be in contact with each other to form a network. The satellite nanoparticles combined to the surface of the porous bead through the functional group exhibit its characteristics well when it has a size ranging from 1 nm to 100 nm, and the nanoparticles may be grown to form a network.

As for fixing of the satellite nanoparticles, the satellite nanoparticles are not fixed through the conventional, general high temperature thermal treatment. Seeds of the satellite nanoparticles are attached to the silica surface and grown at room temperature. When the satellite nanoparticles are grown, covering the organic molecules on the silica surface, so as to be firmly fixed. Thus, it is economical and the process is easy. Also, when the satellite nanoparticles are grown slightly further, the satellite nanoparticles are networked, forming such solid structure that they cannot be separated from the silica surface. The satellite nanoparticles according to an embodiment of the present invention has the structure in which the surface is exposed to its maximum level, so they can be used for a catalyst reaction or as an antivirals, an antimicrobial, or the like.

The satellite nanoparticles may be metal nanoparticles, metal oxide nanoparticles, or semiconductor nanoparticles. The metal nanoparticle may be at least any one selected from the group consisting of Au, Ag, Pt, Pd, Fe, Co, Ni, and an alloy thereof. The metal oxide nanoparticle may be at least any one selected from the group consisting of FeO, $Fe_2O_3$, $Fe_3O_4$, $CoFeO_4$, $NiFeO_4$, $MnFeO_4$, $TiO_2$, $ZrO_2$, $CeO_2$, $Al_2O_3$, and MgO. The semiconductor nanoparticle may be at least any one selected from the group consisting of CdS, CdSe, CdTe, ZnS, ZnSe, ZnTe, GaN, GaP, GaAs, InP, and InAs, or may be a nanoparticle having a core-shell structure including a combination thereof.

One of the key points of the present invention is that the satellite nanoparticles 30 combined with the surface of the porous bead have a substantially uniform size and combined to the functional group through multiple bonding, and since the satellite nanoparticles can make a net structure, they can have a stable structure without dissociation. Nanoparticles combined to the surface of the porous bead exist at the outermost portion of the porous bead-satellite nanoparticles composite and exposed, so they exhibit unique physical, chemical qualities, such as conductivity, anti-bacteria, deodorization characteristics, or the like, of the nanoparticles. Thus, the porous bead-satellite nanoparticles composite can be used as a catalyst in a particular organic reaction or may be used as an antimicrobial or a deodorant.

Meanwhile, the satellite nanoparticles may be combined to the functional group while covering the functional group.

A method for fabricating the porous bead-satellite nanoparticles composite includes (a) introducing porous bead precursor materials to a first solution to prepare a second solution containing the porous bead; (b) introducing a molecule including a functional group at a second end to the second solution to combine a first end of the molecule to an outer surface of the porous bead to prepare a third solution containing a molecule-combined composite; (c) introducing a satellite nanoparticle seed to the third solution to combine the satellite nanoparticle seed to the functional group of the second end of the molecule; (d) growing the satellite nanoparticle seed to prepare a fourth solution containing the porous bead-satellite nanoparticles composite; and (e) recovering the porous bead-satellite nanoparticles composite from the fourth solution. The porous bead precursor material is required for fabricating a porous bead and may be at least one of precursors selected from the group consisting of tetraalkoxy silane, tetraalkoxy titanium, tetraalkoxy zirconium, and tetraalkoxy aluminum forming a silica, titanic, zirconia, alumina, or zeolite porous bead by a sol-gel reaction.

Before step (a), (a') additionally introducing a material including two or more carboxyl groups in the first solution and performing ultrasonic dispersion processing thereon. When a material including two or more carboxyl groups is additionally introduced and dispersed, an excessive clustering phenomenon among the clusters can be prevented.

The growing of the satellite nanoparticles seed in step (d) may be performed by introducing a precursor solution including the component of satellite nanoparticles and a reducing agent into the solution which has undergone step (c) and mixing them, or may be performed until such time as the satellite nanoparticles are grown to come into contact with adjacent satellite nanoparticles to form a network or until such time as the satellite nanoparticles are grown to cover the functional group.

The method for fabricating the porous bead-satellite nanoparticles composite according to an embodiment of the present invention will now be described with reference to the accompanying drawings.

First, an iron oxide nanoparticles cluster was selected as a cluster of super-paramagnetic nanoparticles constituting a core, and was fabricated according to a method described in a document (Angewandte Chemie International Edition 2009, 48, 5875-5879). The iron oxide nanoparticles cluster having an overall diameter of about 300 nm is formed as small iron oxide nanoparticles having a size ranging from 5 nm to 10 nm are clustered, and is quickly responded to an external magnetic field (50~80 $emug^{-1}$). In the present embodiment, the magnetic substance is used as the core of the composite bead to thus allow the finally created porous bead-satellite nanoparticles composite to have magnetism. The magnetic core is not limited to the foregoing iron oxide nanoparticles cluster, and any particles may be used so long as it has super-paramagnetism.

Figure 2:
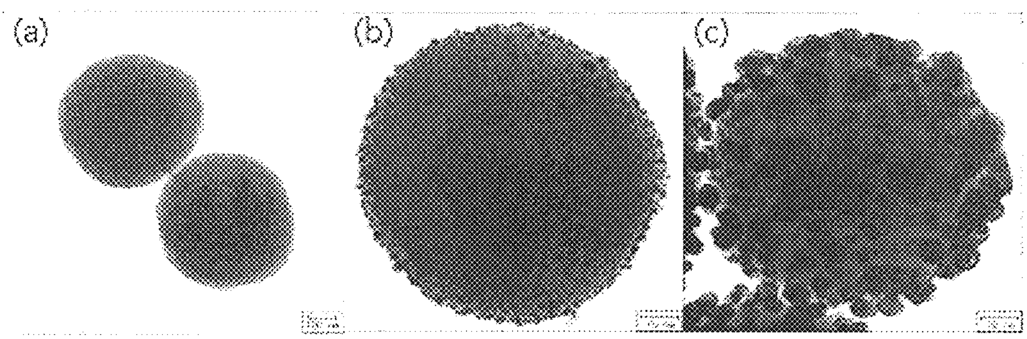
FIG. 2(*a*) is a TEM image of a composite including a cluster of magnetic nanoparticles and a silica porous bead shell covering the cluster of the magnetic nanoparticles, FIG. 2(*b*) is a TEM image of a porous bead-satellite nanoparticles composite including silver satellite nanoparticles combined thereto, and FIG. 2(*c*) is a TEM image of a porous bead-satellite nanoparticles composite including silver satellite nanoparticles of FIG. 2(*b*) grown to be large.

Next, silica is selected as a porous bead material and directly grown on the magnetic core by using a stober method, thus forming a porous bead including the magnetic core and the porous bead shell. A silica shell is formed by using an excessive amount of tetraethoxysilane (TEOS) and silica covering the magnetic substance and silica not covering the magnetic substance are separated by using a magnet, thus selecting only a porous composite bead including the magnetic core and the porous bead shell. As shown in FIG. 2(*a*), the fabricated silica shell has a thickness of about 100 nm and is evenly formed around the magnetic core. When a porous bead shell is fabricated with titanic, zirconia, alumina, zeolite, or the like, instead of silica, a tetraalkoxy compound of each metal may be used.

Trialkoxysilane including an amine group (—$NH_2$) 22 as a functional group, 3-aminopropyltrimethoxysilane, is combined to the surface of the silica shell fabricated thusly to allow the amine group to be exposed from the surface of the silica shell. The nanoparticle is multiple-bonded with the amine groups exposed from the surface. In the present embodiment, in order to combine the gold or silver nanoparticles, the molecules having 3 hydrocarbon atoms, i.e., n=3 in FIG. 1 (21) and including the ends configured as the amine groups are used, but the number of hydrocarbons may change from 2 to 20, and the functional group of the molecules may be selected from among thiol (—SH) and carboxy (—$CO_2H$) as well as amine ($NH_2$).

In order to combine the nanoparticles to the surface of the porous bead shell through amine groups, a silver nanoparticle seed of 1 to 3 nm was synthesized in an aqueous solution by using tetrakis hydroxymethyl phosphoniumchloride (THPC). THPC acts as a reducing agent for reducing gold or silver ions in the aqueous solution and covers the surroundings of the synthesized nanoparticle seed while giving negative electric charges. Thus, the gold or silver nanoparticle seeds reduced by THPC are well dispersed due to the negative electric charges, and when they meet the functional group such as amine which is positively chargeable, they can be strongly combined. The inventors of the present application bonded the gold or silver nanoparticle seeds, which had been reduced by THPC, to the surface of the silica shell through amine group, by using such characteristics. In the reaction of the gold or silver nanoparticle seeds with porous silica bead, an excessive amount of gold or silver nanoparticle seeds were put to be combined to the surface of the porous beads. Remaining gold or silver nanoparticle seeds, which had not been combined to the porous beads, were separated, and only the porous bead to which the gold or silver nanoparticle seeds were combined were used in a next step.

The gold or silver nanoparticle seeds reduced by THPC are too small, having limitation to be used for an industrial purpose. Thus, in order to increase the size of the gold or silver nanoparticle seeds, the inventors of the present invention additionally performed a step of growing satellite nanoparticles centering the seeds. For this end, a silver nitrate solution was mixed in a solution including silica shell with small silver nanoparticles attached thereto, and formaldehyde was slowly added as a reducing agent. Silver ions originated from silver nitrate were reduced to grow around the small silver nanoparticles of 1 to 3 nm, namely, around the silver nanoparticles and has grown to larger silver nanoparticles. S shown in FIG. 2, the size of the finally produced silver satellite nanoparticles could be adjusted by changing the amount of silver nitrate or formaldehyde.

In order to check whether the satellite nanoparticles were dissociated from the surface of the composite, the composite-dispersed solution were processed for two to three seconds in a ultrasonic bath, the composite was separated, and a filtrate was analyzed through atomic absorption spectrometry (AAS). The results showed that the silver component was less than a detection limit (0.2 ppm). Also, according to the results of a catalytic activity experiment, silver nanoparticles included in the porous bead-satellite nanoparticles composite reduced every 4-nitrophenol into 4-aminophenol within 20 minutes, and in comparison, when the reaction was performed under the same conditions without putting the porous bead-silver satellite nanoparticles composite in a comparative experiment, a reduction reaction was never occurred. The composite was recovered by a magnet after the reaction, and the same experiment was repeated five times. The results showed that the composite repeatedly made the reduction reaction successful and properly maintained the activity of the catalyst enough to maintain a reaction speed similar to that of the first reaction. Also, the results of a virus removal experimentation showed that the porous bead-silver satellite nanoparticles composite has a virus removal effect similar to that of an individual silver nanoparticle and can be recovered and reused, and as such, the porous bead-silver satellite nanoparticles composite was confirmed to be environment-friendly and economical. In this manner, the present invention provides the catalyst, antibacterial or anti-viral composite including the foregoing porous bead-silver satellite nanoparticles composite. When the catalyst, antibacterial or anti-viral composite is used, after the catalyst reaction or antibacterial reaction, the porous bead-satellite nanoparticles composite can be easily recovered by providing a magnetic field thereto or by performing centrifugation thereon.

Embodiment

The present invention will be described in detail through embodiments, but such embodiments are presented to help make the present invention clearly understood, and the present invention is not limited thereto.

Embodiment 1

Fabrication of Magnetic Core, Porous Bead Shell, and Porous Bead-Silver Satellite Nanoparticles Composite in which Silver Satellite Nanoparticles were Combined to Surface of Porous Bead Shell (1) First Step: Fabrication of Core Configured as a Cluster of Super-Paramagnetic Nanoparticles According to a method described in the document (Angewandte Chemie International Edition 2009, 48, 5875-5879), $FeCl_3$ (0.65 g, 4.0 mmol) and trisodium citrate (0.20 g, 0.68 mmol) were dissolved in an 20 ml of ethylene glycol, to which sodium acetate (1.20 g) was then added and stirred for 30 minutes. This solution was moved to an autoclave, sealed, and reacted in an oven at temperature of 200° C. for 14 hours to fabricate a core configured as a cluster of super-paramagnetic nanoparticles. This solution was cooled at room temperature, and the cluster was washed with ethanol and distilled water one time, respectively, collected with a magnet and dispersed in 20 ml of ethanol.

(2) Second Step: Synthesis of Magnetic Core-Porous Bead Shell (Composite)

5 ml in 20 ml of the core fabricated in the first step was taken, to which ethanol was added to obtain 0.5 l. 50 ml of distilled water and 0.225 g of trisodium citrate were added, stirred, and processed in an ultrasonic bath for 10 minutes. 15 ml of ammonia water was added to the resultant solution, stirred for one hour, 22.5 ml of TEOS was added, and stirred at 20° C. for 14 hours to fabricate a porous bead (composite) comprised of a magnetic core and a porous bead shell. The solution was centrifuged, a precipitate was washed with ethanol and water, separated with a magnet, and dispersed in 20 ml of ethanol. FIG. 2(*a*) shows a TEM image of the thusly generated magnetic core-porous bead shell (composite).

(3) Third Step: Combining Functional Group (Amine Group) to Surface of Magnetic Core-Porous Bead Shell In order to substitute the surface of the magnetic core-porous bead shell with an amine group, the magnetic core-porous bead shell made in the second step were all dispersed in 100 ml of ethanol, to which 3 ml of ammonia solution, 3 ml of distilled water, and 0.011 ml of aminopropyltrimethoxysilane (APTMS) were added and then stirred for 12 hours. After the reaction was finished, the magnetic core-porous bead shell was washed with ethanol five times by using a magnet recovery method and then dispersed in 20 ml of ethanol.

(4) Fourth Step: Combining Silver Nanoparticles to Surface of Magnetic Core-Porous Bead Shell 1 ml of $AgNO_3$ (1 wt/v %) solution and 5 ml of NaOH solution (0.1 M) were put in 45 ml of water and stirred, to which 0.012 ml of THPC (80 wt %) was slowly mixed to generate silver nanoparticle seeds. 20 ml of the overall silver nanoparticle seed solution was taken and mixed with 5 ml solution of magnetic core-porous bead shell with amine group combined thereto to allow the silver nanoparticle seed to be combined to the amine group of the surface of the porous bead (silca) shell. Remaining silver nanoparticle seeds which have not been combined were separated by using a magnet separation method and discarded. In order to make the small silver nanoparticle seeds grow larger, 5 ml of nanoparticle seed-combined magnetic core-porous bead shell solution was put in an 50 ml of $AgNO_3$ solution (0.01 wt/v %) and stirred. After the two solutions were sufficiently mixed, 0.1 ml of formaldehyde was put thereto to make the silver nanoparticle seed grow larger. FIG. 2(*b*) shows a TEM image of the finally generated porous bead-silver satellite nanoparticles composite, and the silver satellite nanoparticles have a size of 5 to 10 nm. FIG. 2(*c*) shows the silver nanoparticles grown further compared with those of FIG. 2(*b*). The generated silver nanoparticles had a size of about 30 nm and obtained by using 200 ml of $AgNO_3$ solution (0.01 wt/v %) and 0.2 ml of formaldehyde. The fabricated porous bead-silver satellite nanoparticles composite was dispersed in 5 ml of distilled water and used in a following catalytic activity experiment and virus removal experiment.

As for the porous bead-silver satellite nanoparticles composite fabricated in the fourth step, bonding stability between the functional group on the surface of the magnetic porous composite bead and silver nanoparticles was inspected two times. The porous bead-silver satellite nanoparticles composite sufficiently washed five or more times was dispersed in distilled water and processed in an ultrasonic bath for two to three seconds. The porous bead-silver satellite nanoparticles composite was collected by using a magnet and an element analysis of silver component was performed on the supernatant using atomic absorption spectrometry (AAS). It was less than a detection limit (0.2 ppm) of AAS. ICP analysis was performed, and it was 23 ppb and 26 ppb, which satisfies the reference of drinking water. Thus, it was ascertained that the composite according to an embodiment of the present invention does not discharge nanoparticles to an environment, and is an environment-friendly and economical composite material which can be recovered and repeatedly used.

Embodiment 2

Figure 3:
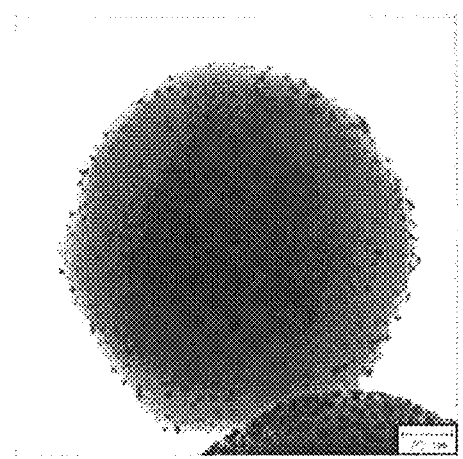
FIG. 3 is a TEM image of porous bead-satellite nanoparticles composite including gold satellite nanoparticles combined thereto.

Fabrication of Magnetic Core, Porous Bead Shell, and Porous Bead-Gold Satellite Nanoparticles Composite in which Gold Satellite Nanoparticles were Combined to Surface of Porous Bead Shell The first to third steps of Embodiment 1 were performed in the same manner, and in the same manner as the fourth step, gold satellite nanoparticles were combined to the surface of the magnetic core-porous bead shell. 2 ml of $HAuCl_4.4H_2O$ (2 wt/v %) solution and 5 ml of NaOH solution (0.1 M) were put in 45 ml of water and stirred, to which 0.012 ml of THPC (80 wt %) was slowly mixed to generate gold nanoparticle seeds. 20 ml of the gold nanoparticle seed solution of the generated overall solution and 2 ml solution of magnetic core-porous bead shell with amine group combined thereto were mixed to allow the small gold nanoparticle seeds to be bonded to the amine group of the surface of the silica shell. The gold nanoparticle seeds on the surface of the magnetic core-porous bead shell was grown to be larger gold nanoparticles (~5 nm) by applying 20 ml of $HAuCl_4.4H_2O$ (0.01 wt/v %) solution and 0.05 ml of formaldehyde and stirring it. FIG. 3 shows a TEM image of the gold nanoparticles.

Embodiment 3

Fabrication of Silica Porous Bead-Silver Nanoparticles Composite without Magnetic Core The first and second steps of Embodiment 1 were omitted, and the third and fourth steps were performed on a silica bead to allow silver nanoparticles to be combined to the surface of the silica bead without a magnetic core therein.

Figure 6:
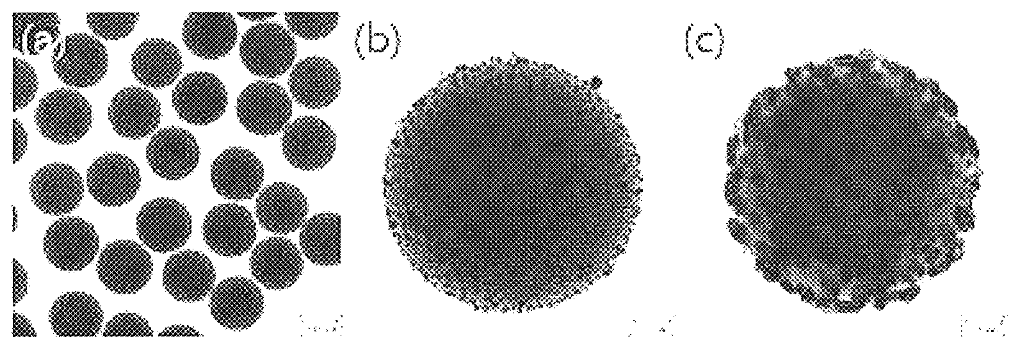
FIG. 6(*a*) is a TEM image of a silica porous bead which does not include a cluster of magnetic nanoparticles, FIG. 6(*b*) is a TEM image of a porous bead-satellite nanoparticles composite including silver satellite nanoparticles combined thereto, and FIG. 6(*c*) is a TEM image of a porous bead-satellite nanoparticles composite including silver satellite nanoparticles of FIG. 2(*b*) grown to be large.

The silica bead was fabricated by using a stöber method, and 50 ml of distilled water and 15 ml of ammonia water were added to 500 ml of ethanol, stirred for one minute, 60 ml of TEOS was added, and stirred at 20° C. for 15 hours. After the reaction was finished, the silica bead was washed with ethanol three times, and dispersed in 1000 ml of ethanol. It was checked that the size of the synthesized silica bead was ~480 nm through a TEM image as shown in FIG. 6(*a*).

In order to attach the silver nanoparticles to the surface of the silica bead, an amine group was combined to the surface of the silica bead in the same manner as the third step in Embodiment 1. For this end, 500 ml of the synthesized silica bead was taken, to which 50 ml of distilled water and 15 ml of ammonia water were added, stirred for one minute, APTMS was added thereto, and then stirred at 20° C. for 15 hours. In this manner, the amine group-combined silica bead was washed with ethanol three times and dispersed in 85 ml of ethanol.

Finally, nanoparticles were combined to the surface of the amine group-combined silica bead in the same manner as the fourth step of Embodiment 1 to fabricate silica bead-silver satellite nanoparticles composite. 10 ml of the silver nanoparticle seed solution was taken and mixed with the 1 ml of amine group-combined silica bead to allow the silver nanoparticle seed to be combined to the amine group on the surface of the silica bead.

Remaining silver nanoparticle seeds which have not been combined were separated by using a centrifugation method and discarded. In order to make the small silver nanoparticle seeds grow larger, 1 ml of nanoparticle seed-combined silica bead solution was mixed in an 50 ml of $AgNO_3$ solution (0.01 wt/v %) and stirred. After the two solutions were sufficiently mixed, 0.02 ml of formaldehyde was put thereto to make the silver nanoparticle seed grow larger. FIG. 6(*b*) shows a TEM image of the finally generated silica bead-silver satellite nanoparticles composite, and the silver nanoparticles have a size of 5 to 10 nm. FIG. 6(*c*) shows the silver nanoparticles grown further compared with those of FIG. 6(*b*). The generated silver nanoparticles have a size of about 30 nm and obtained by using 200 ml of $AgNO_3$ solution (0.01 wt/v %) and 0.08 ml of formaldehyde. The fabricated porous bead-silver satellite had a size of about 30 nm.

Figure 4:
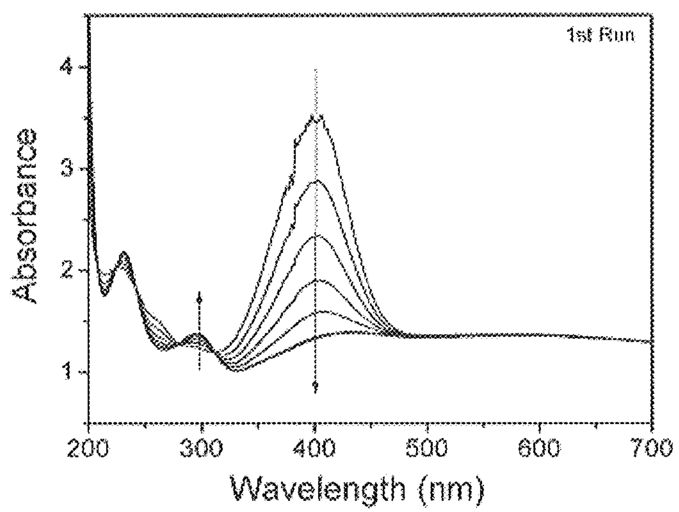
FIG. 4 is a graph of an absorbance showing the progress of a catalyst reaction of the porous bead-satellite nanoparticles composite including silver satellite nanoparticles combined thereto.
Figure 5:
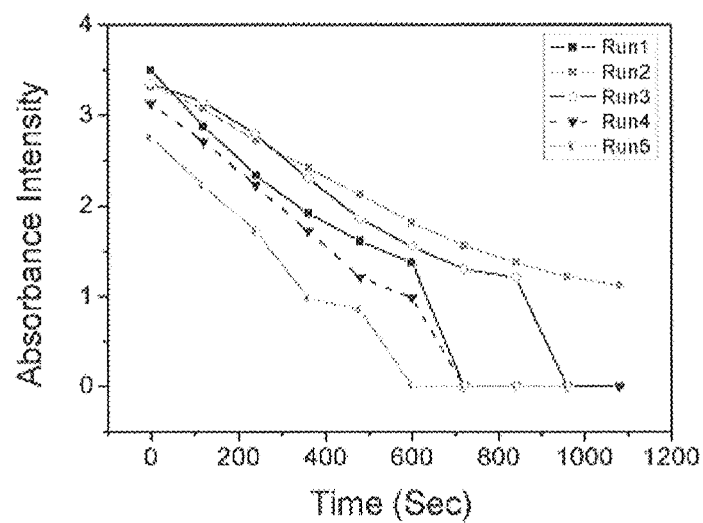
FIG. 5 is a graph showing an 400 nm absorbance measured over time according to reuse after recovery.

Experiment of Catalytic Activity of the Porous Bead-Silver Satellite Nanoparticles Composite As for an experiment of catalytic activity, after 0.2 ml of sodium borohydride solution (30 mM) was put in a 2 ml of 4-nitrophenol solution (0.2 mM), 0.1 ml of porous bead-silver satellite nanoparticles composite (FIG. 2(*b*)) was put thereto as a catalyst, sufficiently shaken, and then observed by UV. A UV spectrum was recorded one time for every two minutes, and after the reaction was finished, the porous bead-silver satellite nanoparticles composite was recovered by a magnet and repeatedly used for the same reactions up to five times. FIG. 4 shows a proceeding state of the reaction when the porous-silver satellite nanoparticles composite was first used. An absorption peak at 400 nm was due to nitro group of nitrophenyl, and as time went by, the reduction reaction was ongoing and the absorbance was reduced, while 290 nm absorbance was increased due to an amino group generated according to the reduction results. Under the experiment conditions, it was observed that every 4-nitrophenol was reduced into 4-aminophenol within 20 minutes, and in a comparative experiment in which a reaction was made under the same conditions without putting the porous bead-silver satellite nanoparticles composite, it was observed that a reduction reaction was never made. FIG. 5 is a graph showing a reaction speed of the catalytic reaction by measuring absorbance at 400 nm over time, in which it is noted that the reaction speed of the porous bead-silver satellite nanoparticles composite was not decreased even it is repeatedly used as a catalyst even up to five times and the reaction could be still completed.

Experiment of Virus Removal of Porous Bead-Silver Satellite Nanoparticles Composite of Embodiment 1

In order to inspect a virus removal function of the porous bead-silver satellite nanoparticles composite having silver nanoparticles having an average 30 nm size combined thereto, a solution in which $1\times10^9$ number of composites was dispersed per 1 ml of distilled water (test sample 1). For comparison, silver nanoparticles having an average 40 nm size were synthesized according to the method disclosed in a document (Analytical Chemistry, 1995, 67, 735-743) to fabricate a solution in which silver $5\times10^{1\circ}$ number of nanoparticles were dispersed per 1 ml of distilled water (test sample 2). 0.5 ml of bacteriophage MS2 ($10^{11}$ PFU/ml), a plant virus, was put in four test tubes, 0.5 ml of the test sample 1 was put in two of the four test tubes and 0.5 ml of the test sample 2 was put in the remaining test tubes, and shaken at 25° C. for five minutes and 30 minutes, respectively. A magnet was placed to the test tubes at a predetermined time to collect the composites, and the amount of virus remaining in filtrate was analyzed. The amount of virus remaining in the filtrate of each test sample was shown in unit of log reduction in Table 1 shown below. It is noted that, when five minutes and 30 minutes have elapsed, the test sample 1 has superior removal potential to that of the test sample 2. In addition, the composite test sample 1 is evaluated to be an excellent material in consideration of the fact that it can be recovered and repeatedly used.

TABLE 1

Virus removal potential of composite and nanoparticle test samples over time

| | 0 minute | 5 minutes | 30 minutes |
|---|---|---|---|
| Test sample 1 (composite) | 0 | −1.01 | −0.91 |
| Test sample 2 (nanoparticles) | 0 | −0.36 | −0.70 |

Some embodiments of the present invention have been described but they are merely illustrative and the present invention is not: limited thereto.

As the present invention may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A porous bead-satellite nanoparticles composite comprising:
- a porous bead;
- molecules each having a first end coupled to the surface of the porous bead and including a functional group on a second end; and
- satellite nanoparticles produced by the following process:
  - (a) couple satellite nanoparticle seeds with size of 1 to 3 nm to the functional group of said molecules;
  - (b) remove unreacted satellite nanoparticle seeds; and
  - (c) grow the coupled satellite nanoparticle seeds to embed the functional group;
- wherein the satellite nanoparticles are not connected to each other, or the satellite nanoparticles are in contact with each other to form networked satellite nanoparticles.

2. The composite of claim 1, wherein the porous bead has a core-shell structure including a cluster core of nanoparticles and a porous bead shell covering the duster core.

3. The composite of claim 2, wherein the nanoparticles constituting the cluster is at least any one selected from the group constituting of FeO, $Fe_2O_3$, $Fe_3O_4$, $CoFeO_4$, $NiFeO_4$, $MnFeO_4$, Fe, Co, Ni, FeCo, and FePt.

4. The composite of claim 2, wherein the cluster core of the nanoparticles has super-paramagnetism.

5. The composite of claim 2, wherein the cluster core of the nanoparticles has a diameter of 50 nm or greater and 1 μm or smaller.

6. The composite of claim 2, wherein the porous bead shell has a thickness ranging from 2 nm to 1 μm.

7. The composite of claim 1, wherein the porous bead is made of at least one selected from the group consisting of silica, titania, zirconia, alumina, and zeolite.

8. The composite of claim 1, wherein the molecule has 2 to 20 hydrocarbon chains, and a functional group of the second end is at least any one selected from the group consisting of an amine group, a thiol group, and a carboxyl group.

9. The composite of claim 1, wherein the satellite nanoparticles are multiple-bonded with the functional group of the second end through the growth of the satellite nanoparticles with embedding both the satellite nanoparticle seeds and the functional group coupled thereon.

10. The composite of claim 9, wherein the satellite nanoparticles are in contact with each other to form a network of the satellite nanoparticles.

11. The composite of claim 1, wherein the satellite nanoparticles are metal nanoparticles, metal oxide nanoparticles, or semiconductor nanoparticles.

12. The composite of claim 11, wherein the metal nanoparticle is at least any one selected from the group consisting of Au, Ag, Pt, Pd, Fe, Co, Ni, and an alloy thereof.

13. The composite of claim 11, wherein the metal oxide nanoparticle is at least any one selected from the group consisting of FeO, $Fe_2O_3$, $Fe_3O_4$, $CoFeO_4$, $NiFeO_4$, $MnFeO_4$, $TiO_2$, $ZrO_2$, $CeO_2$, $Al_2O_3$, and MgO.

14. The composite of claim 11, wherein the semiconductor nanoparticle is at least any one selected from the group consisting of CdS, CdSe, CdTe, ZnS, ZnSe, ZnTe, GaN, GaP, GaAs, InP, and InAs.

15. A catalyst comprising a porous bead-satellite nanoparticles composite of any one of claim 1 to claim 14.

16. An antibacterial or anti-viral composite comprising the porous bead-satellite nanoparticles composite of any one of claim 1 to claim 14.

17. The composite of claim 11, wherein the semiconductor nanoparticle has a core-shell structure wherein the core and the shell are of materials selected from the group consisting of CdS, CdSe, CdTe, ZnS, ZnSe, ZnTe, GaN, GaP, GaAs, InP, and InAs.

* * * * *